(12) United States Patent
Levin

(10) Patent No.: US 6,376,545 B1
(45) Date of Patent: Apr. 23, 2002

(54) DISPERSIBLE COMPOSITIONS CONTAINING L-DOPA ETHYL ESTER

(75) Inventor: Galit Levin, Nordia (IL)

(73) Assignee: Teva Pharmaceutical Industries, Ltd., Petach-Tikva (IL)

(*) Notice: Subject to any disclaimer, the term of this patent is extended or adjusted under 35 U.S.C. 154(b) by 0 days.

(21) Appl. No.: 09/437,699

(22) Filed: Nov. 10, 1999

Related U.S. Application Data
(60) Provisional application No. 60/107,893, filed on Nov. 10, 1998.

(51) Int. Cl.[7] ............ A61K 31/195; A61K 31/24; A61K 31/16; A61K 31/135
(52) U.S. Cl. ............ 514/567; 514/538; 514/614; 514/654; 514/657; 514/960
(58) Field of Search ............... 514/538, 565, 514/567, 614, 654, 657, 960

(56) References Cited

U.S. PATENT DOCUMENTS

| | | | |
|---|---|---|---|
| 3,803,120 A | 4/1974 | Felix | |
| 3,885,026 A | 5/1975 | Heinemann et al. | |
| 3,939,253 A | 2/1976 | Bodor et al. | |
| 3,961,041 A | 6/1976 | Nishimura et al. | |
| 4,035,507 A | 7/1977 | Bodor et al. | |
| 4,663,349 A | 5/1987 | Repta | |
| 4,771,073 A | 9/1988 | Repta | |
| 4,826,875 A | 5/1989 | Chiesi | |
| 4,916,151 A | 4/1990 | Bey et al. | |
| 5,354,885 A | * 10/1994 | Milman et al. | 560/43 |
| 5,525,631 A | 6/1996 | Milman et al. | |
| 5,607,969 A | 3/1997 | Milman et al. | |
| 5,840,756 A | * 11/1998 | Cohen et al. | 514/538 |

FOREIGN PATENT DOCUMENTS

| | | |
|---|---|---|
| EP | 522128 | 1/1992 |
| GB | 1364505 | 8/1974 |

OTHER PUBLICATIONS

Remington's Pharmaceutical Sciences, 1975, Mac Publishing Co. 15th ediction, chapter 89, pp. 1576 to 1607.*

Banerjee et al., "Derivatives of 3,4–Dihydroxyphenylalanine for Peptide Synthesis" J. Org. Chem. (1976) 41(18):3056–3058 (Exhibit 14).

Bodor et al., "Improved Delivery Through Biological Membranes. 4. Prodrugs of L–DOPA" Journal of Medicinal Chemistry (1977) 20(11): 1435–1445 (Exhibit 15).

Cooper et al., "L–DOPA Methyl Ester—A Candidate for Chronic Systemic Delivery of L–DOPA in Parkinson's Disease" Clin. Neuropharmacol. (1984) 7:(1) 89–98 (Exhibit 16).

Cooper et al., "L–DOPA Esters as Potential Prodrugs: Behavioural Acitivity in Experimentation Models of Parkinson's Disease" J. Pharm Pharmacol (Aug. 1987) 39(8): 627–635 (Exhibit 17).

El–Naggar et al., "Synthesis of Some Dipeptides Containing 2–Aminobutyric Acid, 3,4–Dihydroxyphenylalanine, Urea and Thiourea Derivatives" Polish Journal of Chemistry (1978) 52:1809–1814 (Exhibit 18).

Fix et al., "Short–Chain Alkyl Esters of L–DOPA as Prodrugs for Rectal Absorption" Pharm. Res. (1989) 6(6): 501–505 (Exhibit 19).

Juncos et al., "Levodopa Methyl Ester Treatment of Parkinson's Disease" Neurology (1987) 37: 1242–1245 (Exhibit 20).

Lai et al., New Compounds: Synthesis of Alkyl Esters of D,L–DOPA, J. Phar. Sci. (1973) 62: 510–511 (Exhibit 21).

Lou et al., "Direct Enantiomer Separation of Phenylalanine, DOPA and Their Intermediates by Supercritical Fluid Chromatography" Journal of Chromatography (1992) 605: 103–107 (Exhibit 22).

Marrel et al., "L–DOPA Esters as Potential Prodrugs" Eur. J. Med. Chem. (1985) 20(5): 459–465 (Exhibit 23).

Tomiuchi et al., "Enzymatic Reactions in Aqueous–Organic Media. XVII. Optical Resolution of Amino Acid Esters by Enzymatic Hydrolysis in Organic Solvents" Bull. Chem. Soc. Jpn.(1992) 65: 259–2603 (Exhibit 24); and.

Venter et al., "Synthesis Phenylpropanolamine Derivatives as Potentitial β–Adrenergic Agents" S. Afr. Tydskr. Chem (1978) 31(4): 135–137 (Exhibit 25).

* cited by examiner

Primary Examiner—Frederick Krass
Assistant Examiner—Donna Jagoe
(74) Attorney, Agent, or Firm—John P. White; Cooper & Dunham LLP

(57) ABSTRACT

The present invention relates to a dispersible pharmaceutical composition comprising a therapeutically effective amount of L-DOPA ethyl ester, a therapeutically effective amount of a decarboxylase inhibitor, a filler, a disintegrant, and a lubricant. The present invention also provides a method of preparing the pharmaceutical composition described herein.

65 Claims, 6 Drawing Sheets

DISPERSIBLE COMPOSITIONS CONTAINING L-DOPA ETHYL ESTER

This application claims the benefit of U.S. Provisional Application No. 60/107,893, filed Nov. 10, 1998. The content of the above-identified application is hereby incorporated into this application by reference.

Throughout this application, various references are identified by authors and full citations. Disclosure of these publications in their entireties are hereby incorporated by reference into this application to more fully describe the state of the art to which this invention pertains.

BACKGROUND OF THE INVENTION

1. Field of the Invention

The present invention relates to a pharmaceutical composition of a highly purified, stable, non-hygroscopic, crystalline composition of L-DOPA ethyl ester (LDEE). The L-DOPA ethyl ester is a new active ingredient for the treatment of patients suffering from Parkinson's disease and related indications.

2. Description of Related Art

The present invention relates to a novel formulation of L-DOPA ethyl ester that provides a dispersible oral dosage formulation of L-DOPA ethyl ester to result in a fast onset of therapeutic activity in a patient.

L-DOPA, also referred to as levodopa (The Merck Index, Twelfth Edition (1996)), in combination with carbidopa or benserazide, remains one of the most effective therapies for Parkinson's disease (PD). Within five years after initiation of such a therapy, disabling motor fluctuations appear in about 50 percent of the treated patients (Wooten G F (1988). Ann Neurol. 24: 363–365). This disability appears as random periods of sudden and unexpected loss of efficacy of levodopa therapy aggravated with time, and has been termed the 'on-off' phenomenon.

Several studies suggest that the motor fluctuations are directly related to the levels of plasma levodopa (Wooten G F supra). Various observations lend support to this contention, for example, gastric emptying in the elderly, particularly in PD (plasma deficiency) patients, is erratic, often much too slow to compensate for the plasma deficiency in levodopa at the 'end of dose' (Bozeman T, et al., (1990), Am J Gastroenterol 85: 1264 and Kurlan R, et al (1988) Neurology 38: 419–421). This effect, when coupled to the low water solubility of levodopa itself and to the usual retention in the stomach of particulate matter is expected to further decrease the rate of transfer of the ingested dose of levodopa from the gastrointestinal (GI) tract to the plasma (Kelly K A (1981). "Motility of the stomach and gastroduodenal junction", in Johnson L R, editor, Physiology of the Gastrointestinal Tract, Raven Press, New York, pp. 393–410). For almost any drug, the combined pharmacokinetics of a low absorption rate and a high elimination rate (as is the case of levodopa with a plasma half-life of about 1 hour) are conducive to plasma drug levels that are below the effective therapeutic range, hence treatment becomes ineffective.

Various procedures have been sought to remedy this situation. In some cases, direct instillation of a slurry of levodopa through a duodenal tube has given rapid relief from the 'off' state (Kurlan R, et al., (1986) Ann. Neurol. 20: 262–265 and Cedarbaum et al., (1990) Neurology 40: 887–995). In another approach, oral dosing with a dilute aqueous solution of levodopa appeared to be effective (Kurth M C, et al., (1993). Neurology 43: 1036–1039). Neither of these measures are practical enough to allow self-medication when urgently needed. When rapid relief is needed, the more common procedure is to recommend to the patient to crush the levodopa tablet before intake, so as to minimize the time required for its disintegration in the GI tract. The efficacy of this procedure has never been demonstrated.

In an effort to provide pharmaceutical compositions that permit uniform and continuous dissolution of active materials, U.S. Pat. No. 4,259,314 (Lowey, 1981) discloses a composition comprising an active agent in admixture with from 80–95% hydroxypropylmethyl cellulose (HPMC) and 5–206 hydroxypropyl cellulose (HPC) having a moisture content of less than 1%. The formulation described therein is stated to be of use especially with hygroscopic therapeutic agents.

U.S. Pat. No. 5,354,885 (Milman, 1994) discloses a composition containing a solution form of L-DOPA ethyl ester substantially free of L-DOPA suitable for pharmaceutical use. The L-DOPA ethyl ester described therein has been shown to function as a prodrug of levodopa whether delivered by the oral or parenteral route.

There is a need for a pharmaceutical composition that will increase the bioavailability of L-DOPA ethyl ester to a patient requiring such treatment, since the existing compositions do not provide sufficient sustained levels of L-DOPA ethyl ester to maintain a satisfactory level of treatment.

There is a further need to develop a stable solid formulation that will give rapid dissolution of L-DOPA ethyl ester in a dispersible tablet formulation because other methods of administration present a series of limitations and drawbacks. The use of capsules affects dosage, since only single dosage is possible. It is not possible to cut the capsules into halves.

On the other hand, administration in solution form raises a series of drawbacks which may be summarized as follows:

(1) Dosage of the active ingredient requires the use of measuring devices which are not normally precise;

(2) There is limited ease of handling and transport for Parkinson's disease patients due to the volume involved; consequently there is a certain risk that therapy will not be completed, with the consequent loss of efficacy of treatment;

(3) Refrigeration is required and the solution is not stable after more than one year; and (4) It is difficult to produce a solution for human consumption that will contain carbidopa, due to solubility and stability issues.

The subject invention provides a prodrug of L-DOPA to overcome problems such as facilitating their administration by the patient, administering to diabetic patients without additional difficulties, and enhancing the efficacy of treatment.

The development of a tablet formulation presented some unexpected difficulties which arise from the peculiar nature of the active ingredients of the present oral dispersible formulation, namely, the L-DOPA ethyl ester and carbidopa.

First, L-DOPA ethyl ester is not stable at room temperature, and is kept under refrigeration (2–8° C.), whereas the final dispersible tablet formulation should be designed, for optimum convenience to patients, pharmacists and physicians, for storage at room temperature.

Secondly, carbidopa contains 7.5% water. Because L-DOPA ethyl ester is highly sensitive to moisture and undergoes hydrolysis rather easily, the formulation cannot be prepared according to standard methods which comprise direct mixing of all the active ingredients or direct granulation followed by compression into oral tablet formulations. An additional consideration with respect to the high sensitivity of L-DOPA ethyl ester to moisture, is the selection of excipients for mixing in the formulation. The excipients are required to be of low moisture content otherwise the L-DOPA ethyl ester will undergo hydrolysis.

Thirdly, the active ingredients L-DOPA ethyl ester and carbidopa are very reactive towards various excipients. Some excipients ordinarily fungible for many standard formulations could not be used in the present formulation and their selection required exhaustive preformulation screening of many excipients.

This invention provides a solution to the problems referred to above by providing new pharmaceutical formulations which minimize the time required for the tablet disintegration in the gastrointestinal tract. Thereby, the composition of this invention which comprises L-DOPA ethyl ester, carbidopa, microcrystalline cellulose, starch, and magnesium stearate has improved the release of L-DOPA ethyl ester, in turn improving the efficacy of intake.

SUMMARY OF THE INVENTION

The present invention relates to a dispersible pharmaceutical composition comprising a therapeutically effective amount of L-DOPA ethyl ester, a therapeutically effective amount of a decarboxylase inhibitor, a filler, a disintegrant, and a lubricant.

In addition, the present invention provides a method of preparing a dispersible composition, preferably a tablet composition, comprising the steps of:

(a) admixing a therapeutically effective amount of L-DOPA ethyl ester, a pharmaceutically acceptable amount of a filler, and a pharmaceutically acceptable amount of a disintegrant to form a L-DOPA ethyl ester mixture;

(b) granulating a decarboxylase inhibitor mixture comprising a therapeutically effective amount of decarboxylase inhibitor, a pharmaceutically acceptable amount of a disintegrant, and a pharmaceutically acceptable amount of a filler;

(c) admixing the L-DOPA ethyl ester mixture of step (a) and the decarboxylase inhibitor mixture of step (b) with a pharmaceutically acceptable amount of a filler, a pharmaceutically acceptable amount of the disintegrant, and a lubricant; and (d) compressing the admixture of step (c) into dispersible tablets.

This invention also presents a dispersible composition, preferably a tablet composition, comprising L-DOPA ethyl ester and a decarboxylase inhibitor such as carbidopa prepared by the particular method disclosed herein.

This invention further provides a method of treating a patient suffering from Parkinson's Disease and other related indications comprising administering to the patient a therapeutically effective amount of a pharmaceutical composition comprising a therapeutically effective amount of L-DOPA ethyl ester, a therapeutically effective amount of a decarboxylase inhibitor, a filler, a disintegrant, and a lubricant.

BRIEF DESCRIPTION OF THE FIGURES

FIG. 1a: Granulation of L-DOPA Ethyl Ester.

FIG. 1b: Granulation of Carbidopa.

FIG. 1c: Mixture of L-DOPA Ethyl Ester granulate and Carbidopa granulate for Tablet Formation

DETAILED DESCRIPTION OF THE INVENTION

Figure 1A:
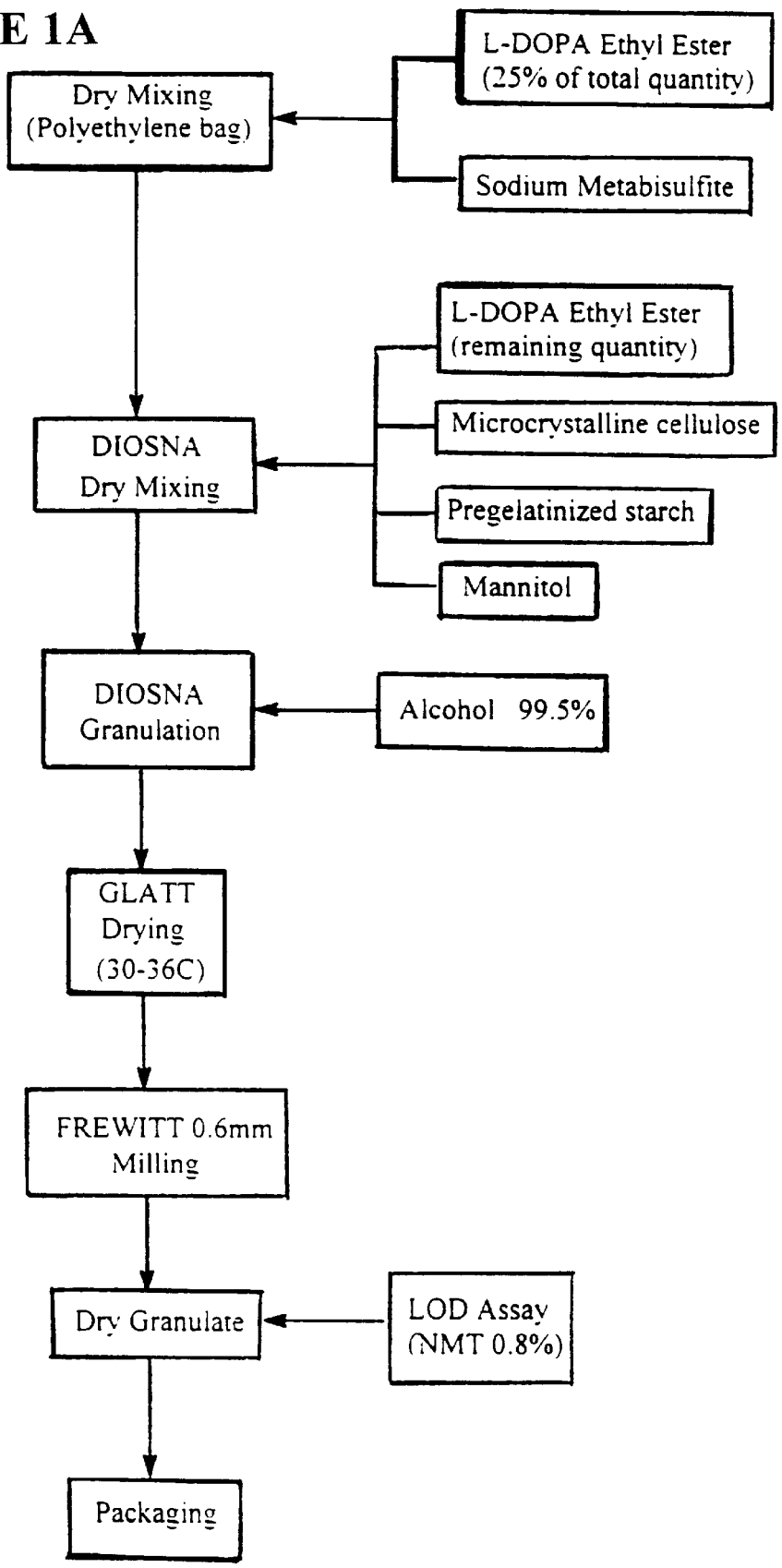
FIGS. 1a–c: Manufacturing Procedure of L-DOPA Ethyl Ester and Carbidopa Dispersible Tablets 114 mg/25 mg for Formulation I.
Figure 1B:
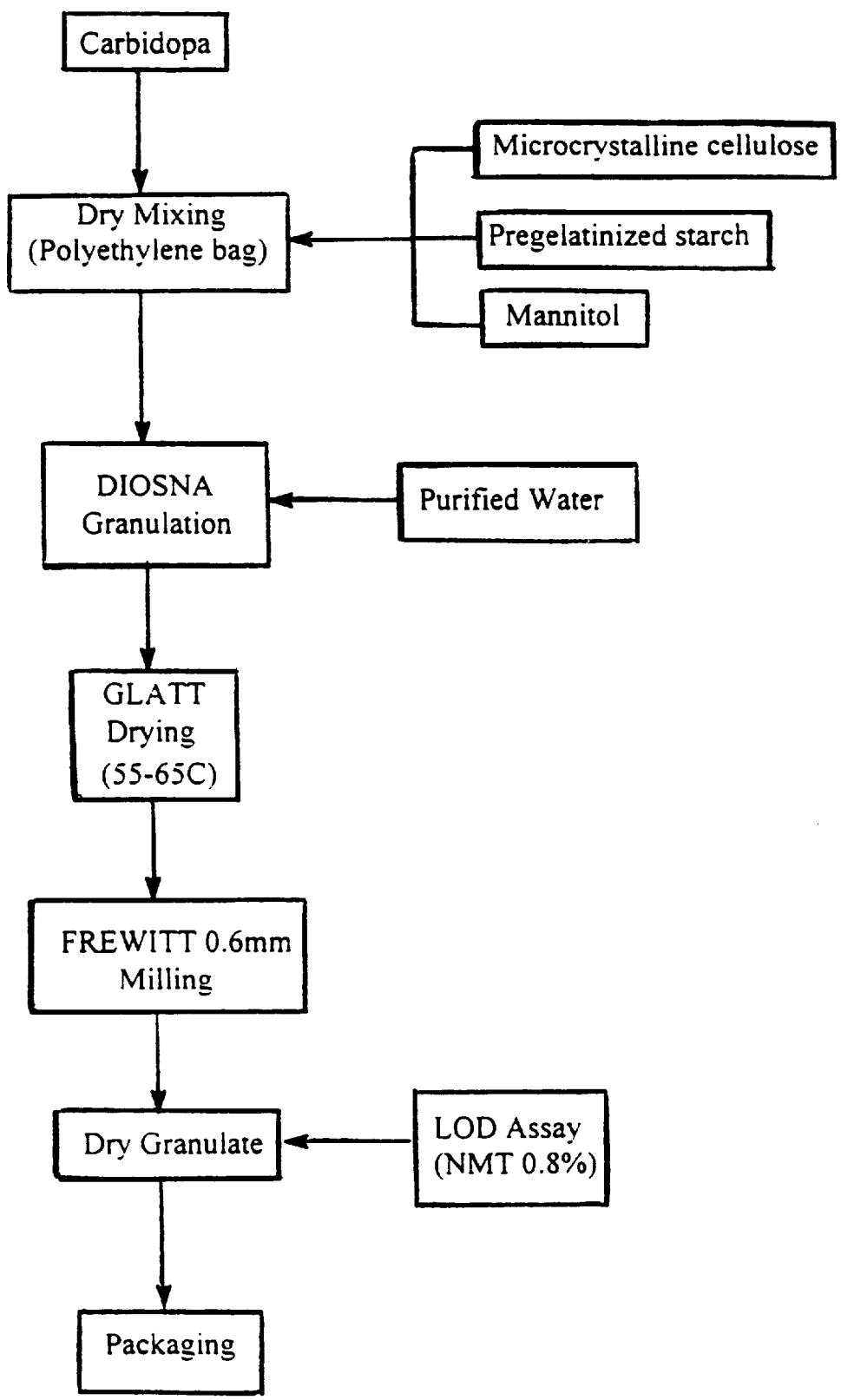
Figure 1C:
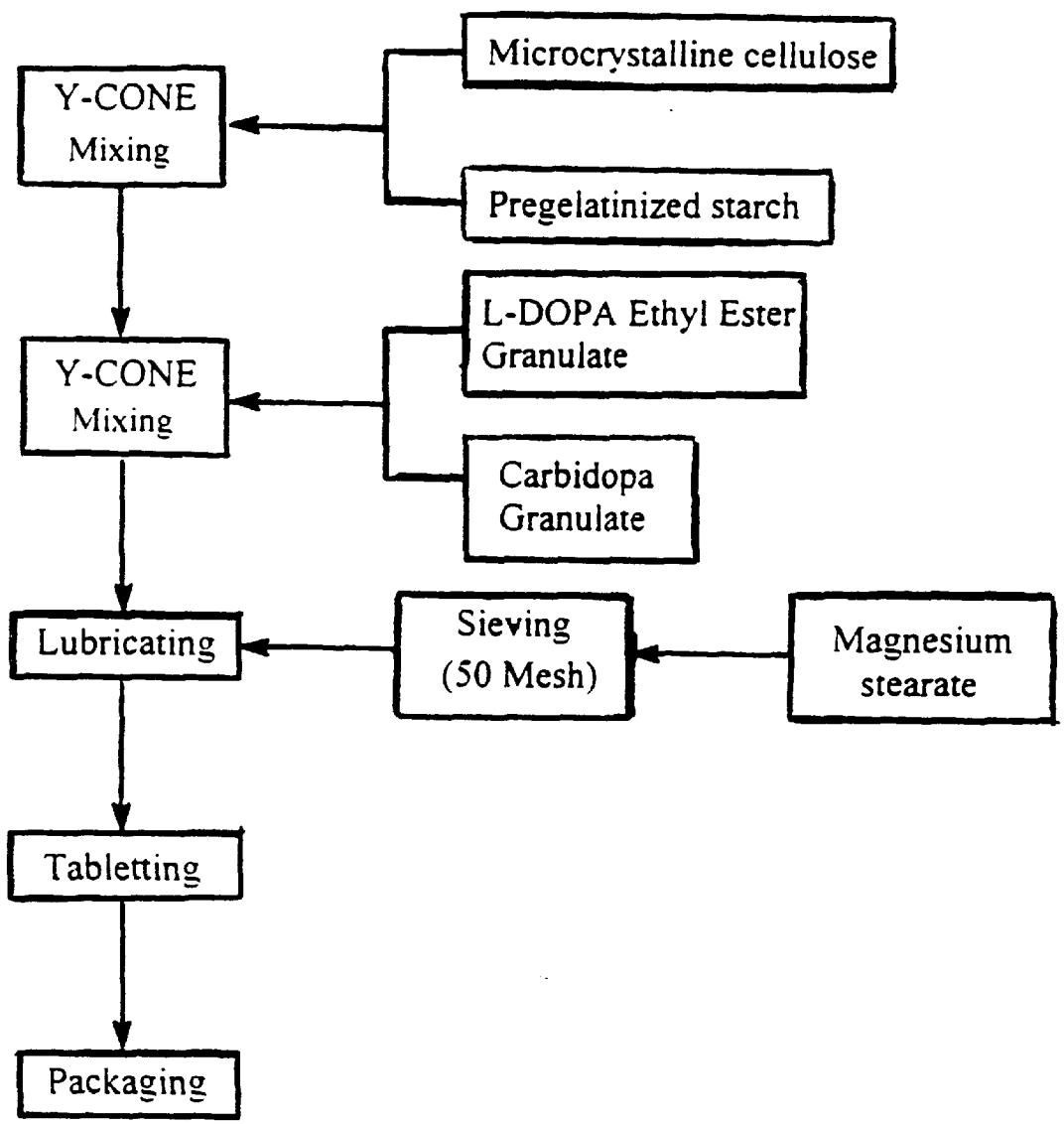
Figure 2:
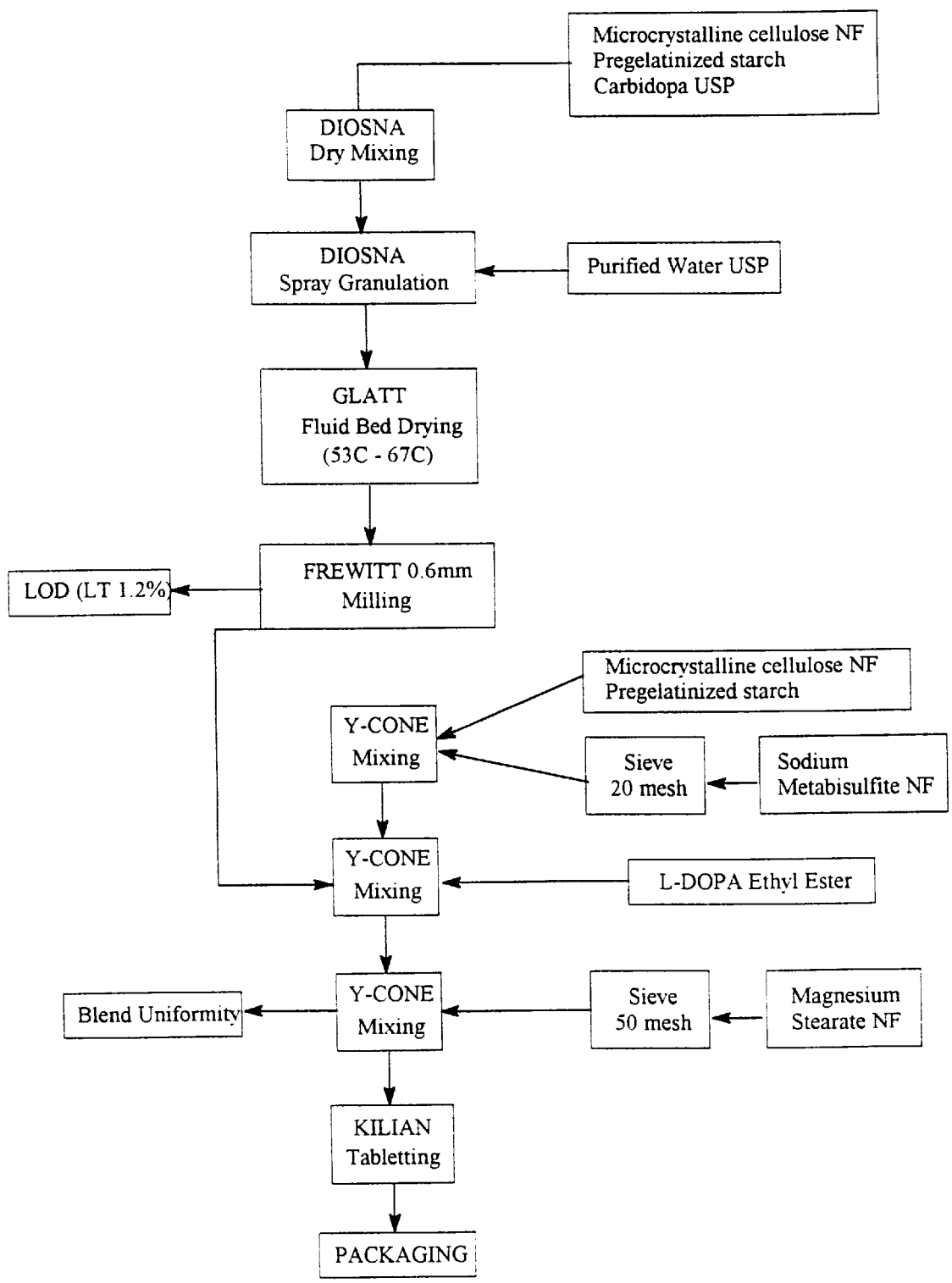
FIG. 2: Manufacturing Procedure of L-DOPA Ethyl Ester and Carbidopa Dispersible Tablets 114 mg/25 mg for Formulation II and III.
Figure 3:
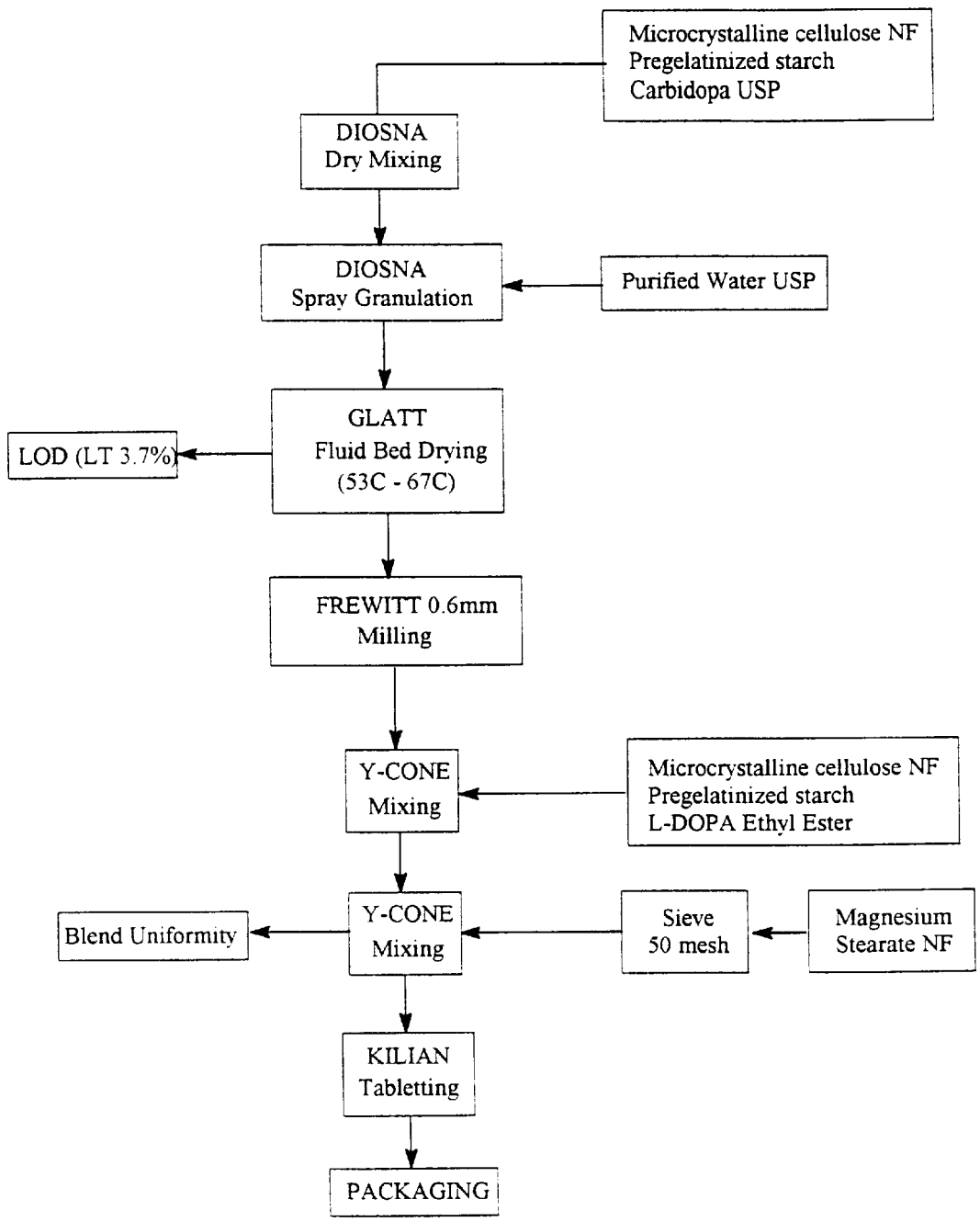
FIG. 3: Manufacturing Procedure of L-DOPA Ethyl Ester and Carbidopa Dispersible Tablets 114 mg/25 mg for Formulation IV and V.

This invention provides a dispersible pharmaceutical composition comprising a therapeutically effective amount of L-DOPA ethyl ester, a decarboxylase inhibitor, a filler, a disintegrant, and a lubricant.

In one embodiment of the invention, the dispersible pharmaceutical composition, preferably a tablet composition, comprises an amount of L-DOPA ethyl ester between 25–50% by weight, an amount of decarboxylase inhibitor between 3.0–10% by weight, an amount of filler between 35–50% by weight, an amount of disintegrant between 3.0–10% by weight, and an amount of lubricant between 0.50–6.0% by weight of the total dispersible composition.

In a specific embodiment of the invention, the decarboxylase inhibitor is carbidopa or benserazide.

In another specific embodiment of the invention, the decarboxylase inhibitor is carbidopa.

In a specific embodiment of the invention, the carbidopa has a moisture content of between 5.0–10.0%.

In another specific embodiment of the invention, the carbidopa has a moisture content of 7.5%.

In one embodiment of the invention, the filler is selected from the group consisting of corn starch, glucose, various natural gums, methylcellulose, carboxymethylcellulose, microcrystalline cellulose, calcium phosphate, calcium carbonate, calcium sulfate kaolin, sodium chloride, powdered cellulose, sucrose, mannitol and starch.

In a specific embodiment of the invention, the filler is a microcrystalline cellulose.

In one embodiment of the invention, the microcrystalline cellulose has a moisture content of up to 5.0%.

In another embodiment of the invention, the microcrystalline cellulose has a moisture content of up to 1.5%.

In one embodiment of the invention, the disintegrant is selected from the group consisting of kaolin, starch, powdered sugar, sodium starch glycolate, crosscarmelose sodium, carboxymethyl cellulose, microcrystalline cellulose and sodium alginate.

In a specific embodiment of the invention, the disintegrant is a pregelatinized starch.

In one embodiment of the invention, the starch has a moisture content of up to 14%.

In another embodiment of the invention, the starch has a moisture content of up to 12%.

In another embodiment of the invention, the starch has a moisture content of up to 7%.

In a further embodiment of the invention, the starch has a moisture content of up to 5%.

In one embodiment of the invention, the amount of lubricant is between 0.50–3.0% by weight of the total dispersible composition.

In one embodiment of the invention, the lubricant is selected from the group consisting of talc, sodium stearyl fumarate, magnesium stearate, calcium stearate, hydrogenated castor oil, hydrogenated soybean oil and polyethylene glycol.

In a specific embodiment of the invention, the lubricant is magnesium stearate.

In one embodiment of the invention, the composition further comprises an excipient.

In another embodiment of the invention, the excipient is a binding agent selected from the group consisting of sorbitol, glucose, xylitol, and mannitol.

In a further embodiment of the invention, the binding agent is xylitol or mannitol.

In a specific embodiment of the invention, the binding agent is mannitol.

In one embodiment of the invention, the composition further comprises an antioxidant.

In another embodiment of the invention, the antioxidant is selected from the group consisting of tocopheral, sodium metabisulphite, butylated hydroxytoluene (BHT), butylated hydroxyanisole (BHA), ascorbic acid and sodium ascorbate.

In a specific embodiment of the invention, the antioxidant is sodium metabisulphite.

In one embodiment of the invention, the dispersible pharmaceutical composition, preferably a tablet composition, comprises L-DOPA ethyl ester in an amount of between 25–50% by weight, carbidopa in an amount of between 3.0–10% by weight, microcrystalline cellulose in an amount of between 35–60% by weight, starch in an amount of between 3.0–10% by weight, magnesium stearate in an amount of between 0.50–3.0% by weight, mannitol in an amount of between 0.0–5.0% by weight, and sodium metabisulfite in an amount of between 0.0–1.0% by weight of the total dispersible composition.

In another embodiment of the subject invention, the dispersible pharmaceutical composition, preferably a tablet composition, comprises L-DOPA ethyl ester in an amount of between 100–300 mg, carbidopa in an amount of between 25–30 mg, microcrystalline cellulose in an amount of between 150–250 mg, starch in an amount of between 15–35 mg, magnesium stearate in an amount of between 0–10 mg, mannitol in an amount of between 0–15 mg, and sodium metabisulfite in an amount of between 0–10 mg for a dispersible composition between 350–600 mg.

In another embodiment of the invention, the microcrystalline cellulose comprises:
  (a) a first microcrystalline cellulose with a moisture content of up to 5%, and
  (b) a second microcrystalline cellulose with a moisture content of up to 1.5%; and the starch comprises:
  (c) a first starch with a moisture content of up to 12%, and
  (d) a second starch with a moisture content of up to 5%.

In a further embodiment of the invention, the dispersible pharmaceutical composition, preferably a tablet composition, comprises microcrystalline cellulose with moisture content of up to 5% in an amount of between 10–25% by weight, microcrystalline cellulose with moisture content of up to 1.5% in an amount of between 20–40% by weight, starch with moisture content of up to 12% in an amount of between 1–5% by weight, and starch with moisture content of up to 5% in an amount of between 1–5% by weight of the total dispersible composition.

In yet a further embodiment of the invention, the dispersible pharmaceutical composition, preferably a tablet composition, comprises microcrystalline cellulose with moisture content of up to 5% in an amount of between 75–85 mg; microcrystalline cellulose with moisture content of up to 1.5% in an amount of between 100–200 mg; starch with moisture content of up to 12% in an amount of between 5–20 mg; and starch with moisture content of up to 5% in an amount of between 3–25 mg for a dispersible composition between 350–600 mg.

In one embodiment of the invention, the dispersible pharmaceutical composition, preferably a tablet composition, comprises L-DOPA ethyl ester in an amount of between 29–48% by weight, carbidopa in an amount of between 4.5–7.2% by weight, microcrystalline cellulose in an amount of between 38–56% by weight, starch in an amount of between 4.7–8.3% by weight, magnesium stearate in an amount of between 0.69–2.1% by weight, mannitol in an amount of between 0.0–2.7% by weight, and sodium metabisulfite in an amount of between 0.0–0.84% by weight of the total dispersible composition.

In yet another embodiment of the invention, the dispersible pharmaceutical composition, preferably a tablet composition, comprises L-DOPA ethyl ester in an amount of between 114–285 mg, carbidopa in an amount of between 25–30 mg, microcrystalline cellulose in an amount of between 200–230 mg, starch in an amount of between 20–32 mg, magnesium stearate in an amount of between 2.6–12 mg, mannitol in an amount of between 0.0–10 mg, and sodium metabisulfite in an amount of between 0.0–2.0 mg for a dispersible composition between 376–390 mg.

In a further embodiment of the invention, the dispersible composition, preferably a tablet composition, comprises microcrystalline cellulose with moisture content of up to 5% in an amount of between 19–22% by weight; microcrystalline cellulose with moisture content of up to 1.5% in an amount of between 30–36% by weight; starch with moisture content of up to 12% in an amount of between 2.0–4.5% by weight; and starch with moisture content of up to 5% in an amount of between 1.0–4.5% by weight of the total dispersible composition.

In yet another embodiment of this invention, the dispersible pharmaceutical composition, preferably a tablet composition, comprises an amount of microcrystalline cellulose with moisture content of up to 5% between 79–80 mg; an amount of microcrystalline cellulose with moisture content of up to 1.5% between 120–135 mg; an amount of starch with moisture content of up to 12% between 8–17 mg; and an amount of starch with moisture content of up to 5% between 4–17 mg for a dispersible composition between 376–384 mg.

In one embodiment of the invention, the dispersible pharmaceutical composition, preferably a tablet composition, comprises L-DOPA ethyl ester in an amount of 30% by weight, carbidopa in an amount of 7.0% by weight, microcrystalline cellulose in an amount of 56% by weight, starch in an amount of 5.4% by weight, and magnesium stearate in an amount of 2.1% by weight of the total dispersible composition.

In a preferred embodiment of the invention, the dispersible pharmaceutical composition, preferably a tablet composition, comprises L-DOPA ethyl ester in an amount of 114 mg, carbidopa in an amount of 27 mg, microcrystalline cellulose in an amount of 214 mg, starch in an amount of 21 mg, and magnesium stearate in an amount of 8.0 mg for a dispersible pharmaceutical composition of 384 mg.

In another embodiment of the invention, the dispersible pharmaceutical composition, preferably a tablet composition, comprises the microcrystalline cellulose with moisture content of up to 5% in an amount of 21% by weight; microcrystalline cellulose with moisture content of up to 1.5% in an amount of 35% by weight; starch with moisture content of up to 12% in an amount of 4.4% by weight; and starch with moisture content of up to 5% in an amount of 1.0% by weight of the total dispersible composition.

In yet another embodiment of the invention, the dispersible pharmaceutical composition, preferably a tablet composition, comprises microcrystalline cellulose with moisture content of up to 56 in an amount of 79 mg; microcrystalline cellulose with moisture content of up to 1.5% in an amount of 135 mg; starch with moisture content of up to 12% in an amount of 17 mg; and starch with moisture content of up to 5% in an amount of 4 mg for a dispersible composition of 384 mg.

In a specific embodiment of the invention, the composition, preferably a tablet composition, has a moisture content of between 2.5% and 3.5%.

This invention also provides a method of preparing a dispersible composition, preferably a tablet composition, comprising the steps of:
 (a) admixing therapeutically effective amount of L-DOPA ethyl ester, a pharmaceutically acceptable amount of a filler, and a pharmaceutically acceptable amount of a disintegrant to form a L-DOPA ethyl ester mixture;
 (b) granulating a decarboxylase inhibitor mixture comprising a therapeutically effective amount of decarboxylase inhibitor, a pharmaceutically acceptable amount of a disintegrant, and a pharmaceutically acceptable amount of a filler;
 (c) admixing the L-DOPA ethyl ester mixture of step (a) and the decarboxylase inhibitor mixture of step (b) with a pharmaceutically acceptable amount of a filler, a pharmaceutically acceptable amount of a disintegrant, and a lubricant; and
 (d) compressing the admixture of step (c) into a dispersible tablet composition.

In one embodiment of the invention, the admixing in step (c) is performed by first mixing the L-DOPA ethyl ester mixture of step (a) with the decarboxylase inhibitor mixture of step (b), then adding the filler, the disintegrant, and the lubricant. The admixing in step (c) is performed by adding the L-DOPA ethyl ester post-granulation.

In one embodiment of the invention, the amount of L-DOPA ethyl ester is between 25–50%, the amount of decarboxylase inhibitor is between 3.0–10%, the amount of filler is between 35–60%, the amount of disintegrant is between 3.0–10%, and the amount of lubricant is between 0.5–3.0% by weight of the total dispersible composition.

In a specific embodiment of the invention, the decarboxylase inhibitor is carbidopa or benzerazide.

In a further specific embodiment of the invention, the decarboxylase inhibitor is carbidopa.

In one embodiment of the invention, the fillers of steps (a), (b), and (c) are selected from a group consisting of corn starch, glucose, various natural gums, methylcellulose, carboxymethylcellulose, microcrystalline cellulose, calcium phosphate, calcium carbonate, calcium sulfate kaolin, sodium chloride, powdered cellulose, sucrose, mannitol and starch.

In another embodiment of the invention, the filler of steps (a), (b), and (c) is a microcrystalline cellulose.

In another embodiment of the invention, the microcrystalline cellulose of step (a) has a moisture content no greater than 5%.

In a further embodiment of the invention, the microcrystalline cellulose of step (b) and (c) has a moisture content no greater than 1.5%.

In one embodiment of the invention, the disintegrant of steps (a), (b), and (c) is selected from a group consisting of kaolin, starch, powdered sugar, sodium starch glycolate, crosscarmelose sodium, carboxymethyl cellulose, microcrystalline cellulose and sodium alginate.

In another embodiment of the invention, the disintegrant of steps (a), (b), and (c) is pregelatinized starch.

In one embodiment of the invention, the lubricant of step (c) is selected from the group consisting of talc, sodium stearyl fumarate, magnesium stearate, calcium stearate, hydrogenated caster oil, hydrogenated soybean oil and polyethylene glycol.

In a specific embodiment of the invention, the lubricant of step (c) is magnesium stearate.

In one embodiment of the invention, the L-DOPA ethyl ester mixture of step (a) and the carbidopa mixture of step (b) further comprises an excipient.

In another embodiment of the invention, the excipient of steps (a) and (b) is a binding agent selected from the group consisting of sorbitol, glucose, xylitol, and mannitol.

In a specific embodiment of the invention, the excipient of steps (a) and (b) is mannitol.

In one embodiment of the invention, the L-DOPA ethyl ester mixture of step (a) further comprises an antioxidant.

In another embodiment of the invention, the antioxidant of step (a) is selected from the group consisting of tocopheral, sodium metabisulphite, butylated hydroxytoluene (BHT), butylated hydroxyanisole (BHA), ascorbic acid and sodium ascorbate.

In a specific embodiment of the invention, the antioxidant of step (a) is sodium metabisulfite.

This invention further provides a method of preparing a pharmaceutical composition, preferably a dispersible tablet composition comprising the steps of:
 (a) admixing a therapeutically effective amount of L-DOPA ethyl ester, a pharmaceutically acceptable amount of a microcrystalline cellulose, and a pharmaceutically acceptable amount of a starch to form a L-DOPA ethyl ester mixture;
 (b) granulating a decarboxylase inhibitor mixture comprising a therapeutically effective amount of carbidopa, a pharmaceutically acceptable amount of a starch, and a pharmaceutically acceptable amount of a microcrystalline cellulose;
 (c) admixing the L-DOPA ethyl ester mixture of step (a) and the carbidopa mixture of step (b) with a pharmaceutically acceptable amount of a microcrystalline cellulose, a pharmaceutically acceptable amount of a starch, and a magnesium stearate; and
 (d) compressing the admixture of step (c) into a dispersible tablet composition.

In one embodiment of the invention, the amount of L-DOPA ethyl ester is between 25–50%, the amount of carbidopa is between 3.0–10%, the amount of microcrystalline cellulose is between 35–60%, the amount of starch is between 3.0–10%, the amount of magnesium stearate is between 0.5–2.5%, and further comprising an amount of an excipient between 0.0–5.0%, and an amount of antioxidant between 0.0–2.5% by weight of the total dispersible pharmaceutical composition, preferably a dispersible tablet composition.

In a further embodiment of the invention, the excipient is a binding agent selected from the group consisting of sorbitol, glucose, xylitol, and mannitol and the antioxidant is selected from the group consisting of tocopheral, sodium metabisulphite, butylated hydroxytoluene, butylated hydroxyanisole, ascorbic acid and sodium ascorbate.

In another embodiment of the invention, the amount of L-DOPA ethyl ester is between 29–48%, the amount of carbidopa is between 4.5–7.2%, the amount of microcrystalline cellulose is between 38–56%, the amount of starch is between 4.7–8.3%, the amount of magnesium stearate is between 0.69–2.1%, the amount of mannitol is between 0.0–2.7%, and the amount of sodium metabisulfite is between 0.0–0.84% by weight of the total dispersible pharmaceutical composition, preferably a dispersible tablet composition.

In a further embodiment of the invention, the amount of L-DOPA ethyl ester is 30%, the amount of carbidopa is 7.0%, the amount of microcrystalline cellulose is 56%, the amount of starch is 5.4%, and the amount of magnesium stearate is 2.1% by weight of the total dispersible pharmaceutical composition, preferably a dispersible tablet composition.

This invention provides a pharmaceutical composition, preferably a dispersible tablet composition prepared by the method, comprising the steps of:
(a) admixing a therapeutically effective amount of L-DOPA ethyl ester, a pharmaceutically acceptable amount of a filler, and a pharmaceutically acceptable amount of a disintegrant to form a L-DOPA ethyl ester mixture;
(b) granulating a decarboxylase inhibitor mixture comprising a therapeutically effective amount of decarboxylase inhibitor, a pharmaceutically acceptable amount of a disintegrant, and a pharmaceutically acceptable amount of a filler;
(c) admixing the L-DOPA ethyl ester mixture of step (a) and the decarboxylase inhibitor mixture of step (b) with a pharmaceutically acceptable amount of a filler, a pharmaceutically acceptable amount of a disintegrant, and a lubricant; and
(d) compressing the admixture of step (c) into a dispersible tablet composition.

This invention also provides a pharmaceutical composition, preferably a dispersible tablet composition prepared by the method comprising the steps of:
(a) admixing a therapeutically effective amount of L-DOPA ethyl ester, a pharmaceutically acceptable amount of a microcrystalline cellulose, and a pharmaceutically acceptable amount of a starch to form a L-DOPA ethyl ester mixture;
(b) granulating a decarboxylase inhibitor mixture comprising a therapeutically effective amount of carbidopa, a pharmaceutically acceptable amount of a starch, and a pharmaceutically acceptable amount of a microcrystalline cellulose;
(c) admixing the L-DOPA ethyl ester mixture of step (a) and the carbidopa mixture of step (b) with a pharmaceutically acceptable amount of a microcrystalline cellulose, a pharmaceutically acceptable amount of a starch, and a magnesium stearate; and
(d) compressing the admixture of step (c) into a dispersible tablet composition.

In one embodiment of the invention, the L-DOPA ethyl ester is L-DOPA ethyl ester derived from pharmaceutically acceptable, crystalline, non-hygroscopic L-DOPA ethyl ester of at least ninety-seven percent purity and containing less than one percent by weight L-DOPA, characterized in that the amount of L-DOPA ethyl ester decreases by less than four percent after one month at forty degrees celsius.

This invention provides a method of treating a patient suffering from Parkinson's Disease and other related indications comprising administering to the patient a therapeutically effective amount of a pharmaceutical composition of the subject invention.

This invention also provides a method of treating a patient suffering from Parkinson's Disease and other related indications comprising administering to the patient a therapeutically effective amount of a pharmaceutical composition comprising a therapeutically effective amount of L-DOPA ethyl ester, a therapeutically effective amount of a decarboxylase inhibitor, a filler, a disintegrant, and a lubricant.

In further embodiments of the invention, any of the above-described compositions are tablets.

The L-DOPA ethyl ester used in the compositions of the present invention is preferably that as described in U.S. Pat. No. 5,354,885, the contents of which are hereby incorporated by reference, and is prepared according to the method described therein. Preferably the L-DOPA ethyl ester is highly purified, stable non-hygroscopic and crystalline. The therapeutically effective amount of L-DOPA ethyl ester is preferably an amount of from 10 to 1,000 milligram equivalents of levodopa or more preferably, the therapeutically effective amount of L-DOPA ethyl ester is from 50 to 250 milligram equivalents of levodopa.

The conditions under which the composition is compressed will influence the final characteristics of the composition. The techniques for compression of the composition into a dispersible oral dosage form such as a dispersible tablet are known in the art. See for example, U.S. Pat. No. 3,885,026 and European Patent No. 0 522 128 B1 relating to dispersible tablet preparations and U.S. Pat. No. 4,680,323, for general guidance on formulations, the entire contents of which patents are hereby expressly incorporated by reference to more fully describe the state of the art.

The final products may additionally contain other adjuvants such as stabilizers, preservatives, coloring agents or binding agents and therefore the subject invention is not limited to the adjuvants specifically claimed.

As described supra, the dispersible formulations such as a dispersible tablet of L-DOPA ethyl ester and carbidopa described in the present invention have not been disclosed in the literature. The L-DOPA ethyl ester composition is highly stable and nonhygroscopic such that the L-DOPA ethyl ester content remains at least 97% by weight of the active ingredient after incubation for 6 months at 40° C. Further, the L-DOPA ethyl ester may be present in the composition as a free base.

While the present invention is novel, the formulation presented some unexpected experimental difficulties which have been successfully overcome as disclosed herein. Selection of various excipients for tablet formulation with L-DOPA ethyl ester and carbidopa must take into account the properties of these active ingredients in order to form a stable dispersible tablet.

This invention will be better understood from the Experimental Details which follow. However, one skilled in the art will readily appreciate that the specific methods and results discussed are merely illustrative of the invention as described more fully in the claims which follow thereafter.

Experimental Details

I. Experimentation with Proportions of L-DOPA Ethyl Ester and Constituents for Tablet Formulation General Description of the Formulation Initially, the product was formulated as a mixture of two granulates: a L-DOPA ethyl ester granulate and a Carbidopa granulate, because Carbidopa contains 7–8% water while L-DOPA ethyl ester is sensitive to moisture.

TABLE 1

Constituents included in the L-DOPA Ethyl Ester and Carbidopa Dispersible Tablets

| Constituents | Specification | Quantity per Tablet (mg) |
|---|---|---|
| ACTIVE INGREDIENTS | | |
| L-DOPA Ethyl Ester | As described in U.S. Pat. No. 5,354,885. | 114.0 |
| Carbidopa | USP | 27.0* |
| INACTIVE INGREDIENTS | | |
| Microcrystalline cellulose (≦5% moisture content) | NF | 75.0–80.0 |
| Starch (≦12% moisture content) | NF | 8.0–17.0 |
| Microcrystalline cellulose (≦1.5% moisture content) | NF | 120.0–150.0 |
| Starch (≦5% moisture content) | NF | 4.0–20.0 |
| Mannitol | NF | 0.0–10 |
| Sodium Metabisulfite | NF | 0.0–5.0 |
| Magnesium Stearate | NF | 2.6–12.0 |

*27.0 mg carbidops USP (monohydrate) is equivalent to 25.0 mg carbidopa USP (anhydrous).

The general procedure for preparing a formulation of L-DOPA ethyl ester and carbidopa can be described as the following. Two different compositions A and B were separately prepared, to be used for formulating active ingredients L-DOPA ethyl ester and carbidopa, respectively. In each case, the filler composition was prepared by mixing the components in the desired proportion in a mixing bowl. The mixture was thoroughly stirred to achieve a uniform consistency. A desired amount of carbidopa was added to filler composition A and the mixture was granulated. A desired amount of L-DOPA ethyl ester was added to filler composition B and the mixture was granulated in Formulation I only. For the method for producing Formulations II, III, IV, and V, only the carbidopa mixture was granulated.

The mixtures and/or granules of compositions A and B were mixed together with another filler composition, composition C and formulated into dispersible tablets according to standard techniques on standard equipment under standard conditions known in the art. Coloring agents, sweeteners and other formulation additives can be added when desired and at appropriate stages of the formulation according to standard industry practices, taking into consideration the above-discussed specific peculiarities of the active ingredients L-DOPA ethyl ester and carbidopa.

The ingredients of compositions A, B and C are listed as below:

Composition A (Carbidopa Granulate)
  27 mg Carbidopa USP
  80 mg microcrystalline cellulose with ≦5% moisture content
  8 mg starch with ≦12% moisture content
  8 mg Mannitol USP/NF (optional)

Composition B (L-DOPA Ethyl Ester Granulate or Mixture)
  114 mg L-DOPA ethyl ester
  20 mg microcrystalline cellulose with ≦1.5% moisture content (16.66% of total microcrystalline cellulose)
  2 mg Sodium Metabisulfite (optional)
  2 mg starch with ≦5% moisture content (11.76% of total starch)
  2 mg Mannitol USP/NF (optional)

Composition C (Final Mixture)
Granulates of Composition A and Granulates/mixture of Composition B are Mixed with:
  100 mg microcrystalline cellulose with ≦1.5% moisture content (83.34% of total microcrystalline cellulose)
  15 mg starch with ≦5% moisture content (88.24% of total starch)
  3.8 mg Magnesium Stearate This invention describes five examples of L-DOPA ethyl ester and carbidopa formulations. Dispersible tablets were prepared from the following pharmaceutical formulations:

| Formulation I | | |
|---|---|---|
| Constituents | Batch A | Batch B |
| microcrystalline cellulose (≦5% moisture content) | 80.0 mg | 80.0 mg |
| Starch (≦12% moisture content) | 8.0 mg | 8.0 mg |
| Carbidopa USP | 27.0 mg | 27.0 mg* |
| Mannitol | 10.0 mg | 10.0 mg |
| microcrystalline cellulose (≦1.5% moisture content) | 120.0 mg | 120.0 mg |
| Starch (≦5% moisture content) | 12.0 mg | 17.0 mg |
| Sodium Metabisulfite NF | 2.0 mg | 2.0 mg |
| L-DOPA Ethyl Ester | 114.0 mg | 114.0 mg |
| Magnesium Stearate NF | 2.6 mg | 3.78 mg |
| Tablet weight | 375.6 mg | 381.78 mg |

| Formulation II | |
|---|---|
| microcrystalline cellulose (≦5% moisture content) | 79.0 mg |
| Starch (≦12% moisture content) | 17.0 mg |
| Carbidopa USP | 27.0 mg* |
| microcrystalline cellulose (≦1.5% moisture content) | 124.0 mg |
| Starch (≦5% moisture content) | 15.0 mg |
| Sodium Metabisulfite NF | 2.0 mg |
| L-DOPA Ethyl Ester | 114.0 mg |
| Magnesium Stearate NF | 5.7 mg |
| Tablet weight | 383.7 mg |

| Formulation III | |
|---|---|
| microcrystalline cellulose (≦5% moisture content) | 79.0 mg |
| Starch (≦12% moisture content) | 17.0 mg |
| Carbidopa USP | 27.0 mg* |
| microcrystalline cellulose (≦1.5% moisture content) | 135.0 mg |
| Starch (≦5% moisture content) | 4.0 mg |
| Sodium Metabisulfite NF | 2.0 mg |
| L-DOPA Ethyl Ester | 114.0 mg |
| Magnesium Stearate NF | 5.7 mg |
| Tablet weight | 383.7 mg |

| Formulation IV | |
|---|---|
| microcrystalline cellulose (≦5% moisture content) | 79.0 mg |

-continued

| Constituents | |
|---|---|
| Starch (≦12% moisture content) | 17.0 mg |
| Carbidopa USP | 27.0 mg* |
| microcrystalline cellulose (≦1.5% moisture content) | 135.0 mg |
| Starch (≦5% moisture content) | 4.0 mg |
| L-DOPA Ethyl Ester | 114.0 mg |
| Magnesium Stearate NF | 5.7 mg |
| Tablet Weight | 381.7 mg |

Formulation V

| Constituents | Batch A | Batch B |
|---|---|---|
| L-DOPA Ethyl Ester | 114.0 mg | 28.5 mg |
| Carbidopa USP | 27.0* mg | 6.75 mg |
| microcrystalline cellulose (≦5% moisture content) | 79.0 mg | 19.75 mg |
| Starch (≦12% moisture content) | 17.0 mg | 4.25 mg |
| microcrystalline cellulose (≦1.5% moisture content) | 135.0 mg | 33.75 mg |
| Starch (≦5% moisture content) | 4.0 mg | 1 mg |
| Magnesium Stearate NF | 8.0 mg | 2 mg |
| Tablet Weight | 384.0 mg | 96 mg |

*27.0 mg Carbidopa USP (monohydrate) is equivalent to 25.0 mg Carbidopa USP (anhydrous).

For the above Formulations, the antioxidant (sodium metabisulfite) and the binding agent (mannitol) are optional. Also, use of starches and microcrystalline cellulose are not limited to the particular moisture contents specified above. However, high moisture excipients such as a starch with over 12% water are less preferable because it will affect the stability of the tablet. Formulation III has also been formulated using a microcrystalline cellulose with a moisture content of up to 5%. An alternative lubricant that may be used in the Formulations is sodium stearyl fumarate. The tested optimum percentage of sodium stearyl fumarate in the tablet composition was between 2.0 to 5.0%.

Formulation I shows two trials of the composition of a dispersible tablet formulation wherein L-DOPA ethyl ester and carbidopa are present at 114 mg and 27 mg, respectively. In pursuit of improving the pharmaceutical properties and the stability of the tablets, the production procedure was simplified and an excipient was eliminated.

To simplify the production procedure, granulation of L-DOPA ethyl ester was eliminated. Formulation I is the only formulation of the five examples in which both the carbidopa mixture and the L-DOPA ethyl ester mixture are granulated in formulation of the tablet. In Formulations II to V only the carbidopa mixture is granulated in formulation of the tablet. The results of the experiment show that the process for Formulation II and III is easier, less wasteful, less costly and less potentially destabilizing of the active ingredient. To improve the stability of the tablet, the mannitol from Formulation I was eliminated from Formulations II and III.

Further experiments to improve the formulation without changing the excipients and retaining a similar disintegration time to Formulation II, yielded Formulation III. The difference between Formulations II and III is the amount of microcrystalline cellulose (≦1.5% moisture content) in relation to the amount of starch (≦5% moisture content).

The tablet was further improved in Formulation IV from Formulation III, since Formulation IV does not contain any sodium metabisulfite which is known to cause allergic reactions or irritations. The stability results show that Formulation IV is stable without the antioxidant.

Finally, Formulation V has greater amounts of magnesium stearate than Formulation IV. The increase in lubricant enables tabletting at higher machine speeds. Also, this elevation in lubricant did not change the disintegration or dissolution times. Formulation V is preferred over Formulation IV because the amount of magnesium stearate (lubricant) in Formulation V is greater and therefore the tablets prepared according to this formulation break up less.

Stability reports of Formulation I (Batch A and Batch B) in 25° C./60% RH and 40° C./75% RH show a peak at RRT=0.6 which was found to be an interaction product between LDEE and Mannitol. Formulations II, III, IV and V do not contain Mannitol and therefore this peak does not appear.

The stability reports for the subject tablets confirm the formulation of a successful dispersible tablet. The moisture content of the tablets after production is 2.5 to 3.5%. The disintegration occurs in less than one minute and more than 90% dissolution of the tablet occurs in 5 minutes.

Fillers such as Avicel® PH 101, Avicel® PH 102, and Avicel® PH 112 manufactured by FMC Corporation, are microcrystalline cellulose binders and were employed in the experiments for tablet formulation. The three different kinds of microcrystalline cellulose binders mentioned above differ in moisture content. Avicel® PH 101 and Avicel® PH 102 are both high moisture content microcrystalline cellulose binders having less than or equal to 5% moisture content. Avicel® PH 112 is a low moisture content microcrystalline cellulose binder having less than or equal to 1.5% moisture content.

Disintegrants such as Starch 1500 and Starch 1500 LM manufactured by Colorcon Limited, are pregelatinized starches and were also employed in the experiments for tablet formulation. The two different kinds of pregelatinized starches mentioned above differ in moisture content. Starch 1500 is a regular moisture content pregelatinized starch having less than or equal to 12–14% moisture content. Starch 1500 LM is a low moisture content pregelatinized starch having less than or equal to 5–7% moisture content.

II. Dissolution Test for L-DOPA Ethyl Ester/Carbidopa Dispersible Tablets

Methodology

The dissolution of L-DOPA ethyl ester and carbidopa dispersible tablets was measured in water at room temperature according to the following methodology which was designed to simulate the administration of these tablets to patients. The recommended use is to place a tablet (384 mg) for a few seconds in about 100 mls of water, and to dissolve while swirling or stirring. The suspension should be drunk within 30 minutes.

In order to automate the measurement, a USP 6-Pot Dissolution Apparatus is used. Each of 6 tablets are dissolved in 100 ml of purified water in a 200 ml vessel at room temperature (23±2° C.). This is the minimum volume which may be used with the USP Dissolution Apparatus. The solutions are stirred with paddles rotating at 200 rpm, which simulates the turbulence caused when the solution is stirred in a cup, with a teaspoon. After 5 minutes of stirring, samples were withdrawn from each vessel and are analyzed by reversed-phase high performance liquid chromatography with UV detection.

In this experiment specifically, the amount of L-DOPA ethyl ester or carbidopa is determined by using a 10 cm C18 column, based on 3μ-diameter spherical silica particles with 100 Å pore size. The elution solvents comprise a gradient of acetonitrile and phosphate buffer with ion-pairing reagent (at pH 2.7). The detection technique is ultraviolet absorption at 280 nm, the wavelength of maximum absorption for both L-DOPA ethyl ester and Carbidopa.

The test provides important information on the dissolution of both L-DOPA ethyl ester and carbidopa from this dosage form, and should be applied during stability studies, at least during the development stages of the formulation.

Results of the experiments testing dissolution of tablets are shown in Table 2 below:

TABLE 2

Percentage of Dissolution of L-DOPA Ethyl Ester and Carbidopa Tablets

|  | 1 minute | 2 minutes | 5 minutes |
|---|---|---|---|
| L-DOPA Ethyl Ester | 67.2% | 90.1% | 102.7% |
| Carbidopa | 64.3% | 87.6% | 101.4% |

III. Pharmacokinetic Study in Advanced Parkinson's Disease Patients

Objective

To compare the pharmacokinetic profiles of levodopa and carbidopa following a single dose administration of four different treatments:

1. L-DOPA Ethyl Ester oral solution with Carbidopa tablet
2. L-DOPA Ethyl Ester/Carbidopa dispersible tablet (dissolved in water)
3. L-DOPA Ethyl Ester/Carbidopa dispersible tablet (swallowed whole)
4. Levodopa/Carbidopa standard tablet in Parkinson's disease patients who developed significant fluctuations after chronic levodopa therapy.

Study Design

This was a pharmacokinetic, open label, randomized, four-way crossover study to compare the pharmacokinetic profiles of four treatments.

Each patient was randomly assigned to receive a sequence of four treatments. Each patient was to complete his/her sequence of four treatments within two weeks where only a single treatment per day was allowed and a 48 hours interval between treatments was mandatory.

Twenty nine (29) patients entered the trial and received each of the four treatments described above. Only the morning dose, which was originally levodopa/carbidopa standard tablet, was replaced by one of the four treatment options in each of the four treatment days.

Each patient continued his/her own levodopa/carbidopa dosage regimen. Thus, the replaced morning study drug dose was equivalent to the individual levodopa/carbidopa dose for each patient.

Pharmacokinetic evaluation was performed by determination of the plasma levels of levodopa, carbidopa and L-DOPA Ethyl Ester. All patients were subjected to this evaluation on each of the four treatment days. Blood samples were taken before dosing and 5, 15, 30, 45, 60, 90, 120 and 240 minutes thereafter. In addition, the time for the drug to act or for the patient to become mobile, e.g. the "time to on", was recorded following each drug administration.

At each visit, patients were evaluated for adverse events, vital signs, and concomitant medication. Clinical laboratory assessments were performed at the first and at the last visit.

Population

Patients had to be diagnosed as having Parkinson's disease with significant response (on/off) fluctuation following chronic levodopa/carbidopa therapy for at least one year. The severity of the disease has to be determined according to Hoehn and Yahr staging (stage 2–5 during off). Patients with response fluctuations are the target population for the use of L-DOPA ethyl ester.

PK Assessment

The assessment was based on plasma level determination of levodopa, carbidopa and L-DOPA Ethyl Ester and on the time for each dose to reach the maximal blood level concentration ($T_{max}$).

The results of the study are summarized in Table 3 below.

TABLE 3

Levodopa Pharmacokinetic Parameters in Advanced-stage Parkinson's Disease Patients (mean ± SD; n = 26)

|  | L-DOPA Ethyl Ester Solution/ Carbidopa Tablets | L-DOPA Ethyl Ester/ Carbidopa Tablets Dissolved | L-DOPA Ethyl Ester/ Carbidopa Tablets Swallowed | L-DOPA/ Carbidopa Standard Tablets |
|---|---|---|---|---|
| $T_{max}$ (min.) | 28 ± 18** (median = 15) | 29 ± 21* (median = 23) | 32 ± 17* (median = 30) | 54 ± 36 (median = 45) |

*p < 0.01 (vs. LD/CD);
**p < 0.001 (vs LD/CD)

IV. L-DOPA Ethyl Ester Degradation in Solution (4° C.), Tablets (25° C./60% RH), and Tablets (40° C./75% RH).

A comparison of L-DOPA ethyl ester (LDEE) degradation in LDEE oral solution (4° C.), and in two environmental conditions of LDEE and Carbidopa dispersible tablets (at 25° C./60% RH and at 40° C./75% RH), was performed by measuring the change in levels of L-DOPA in samples over a six month period of time. L-DOPA is the main degradation product of L-DOPA ethyl ester. Elevation in the level of L-DOPA indicates degradation of LDEE.

Figure 4:
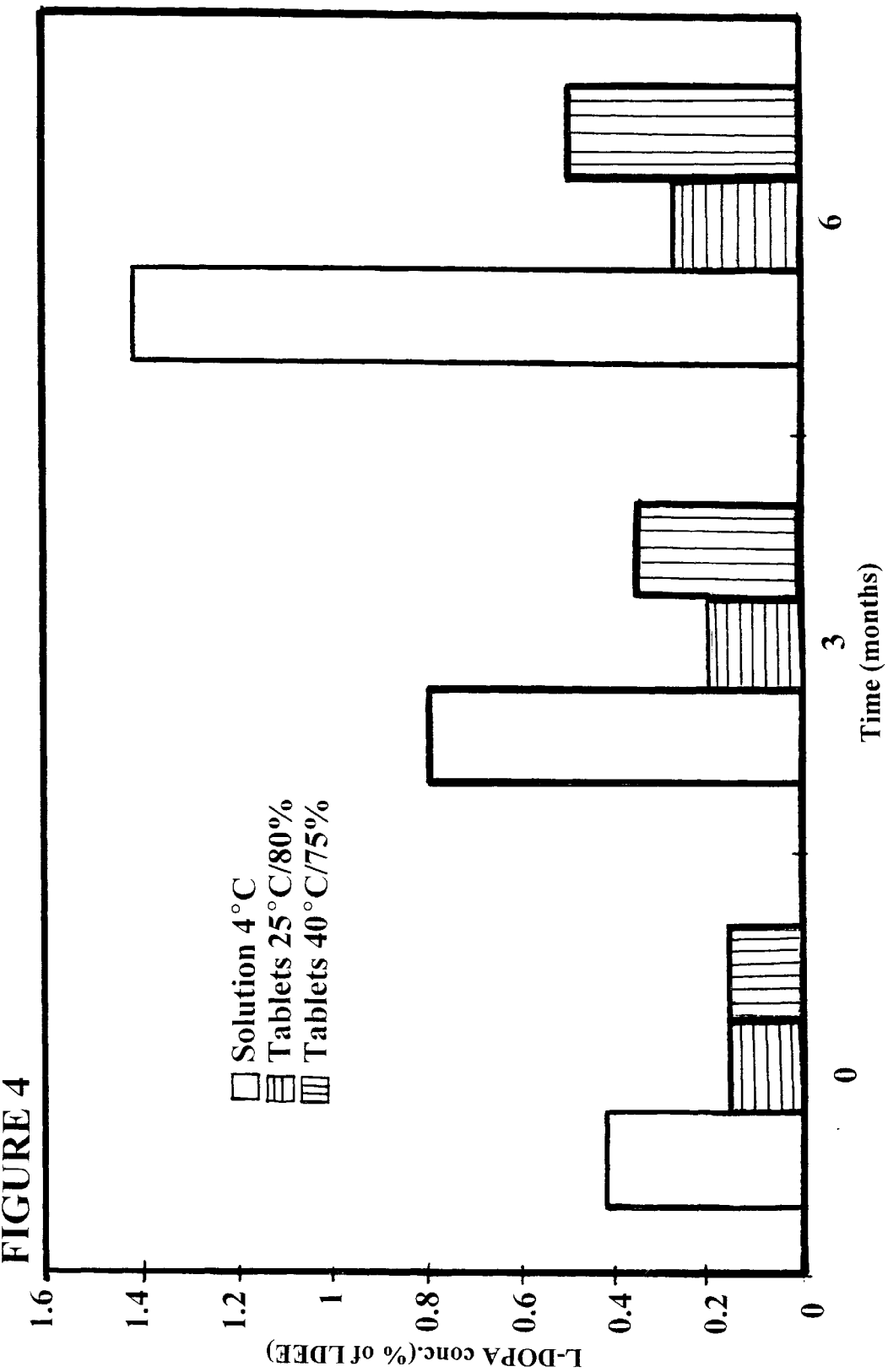
FIG. 4: Comparison of L-DOPA Ethyl Ester Degradation in Solution (4° C.), Tablets (25° C./60% RH), and Tablets (40° C./75% RH) Via Measurement of Change in Levels of L-DOPA over a Six Month Period.

The change in the level of L-DOPA with time, expressed as percent of the concentration of LDEE in the sample, was determined in LDEE and Carbidopa Dispersible Tablets (Formulation V, packed in aluminum blisters) and in LDEE oral solution (packed in PET bottles) The composition of the solution was (per 1 ml): 57.1 mg LDEE, 1.2 mg Methylparaben, 1.6 mg Saccharin sodium, 0.1 mg Edetate disodium and cherry flavor. The solution was acidified with HCl to pH 4.0, in which the stability of LDEE is maximal. The solution was kept in refrigeration (4° C.) while the tablets were kept at room conditions (25° C. and 60% relative humidity) or in accelerated stability conditions (40° C. and 75% relative humidity). The results are shown below in Table 4 and in FIG. 4:

TABLE 4

Concentration of L-DOPA (as % of the concentration of LDEE) in Solution (4° C.), and in Tablets (at 25° C./60% RH and at 40° C./75% RH) at Three Month Intervals over a Six Month Period of Time

|  | Months | | |
|---|---|---|---|
|  | 0 | 3 | 6 |
| Solution (4° C.) | 0.41 | 0.79 | 1.41 |
| Tablets (25° C./60% RH) | 0.15 | 0.19 | 0.26 |
| Tablets (40° C./75% RH) | 0.15 | 0.34 | 0.49 |

The elevation in the concentration of L-DOPA in the tablets was much slower than in the solution, even though the tablets were kept at higher temperatures (which accelerate chemical reactions).

In conclusion, the results demonstrate that the formulation of the dispersible tablets brings about a much better stability of LDEE than in solution. This stability enables storage of the tablets at room temperature instead of in refrigeration, which is more convenient for patients.

What is claimed is:

1. A dispersible tablet comprising a therapeutically effective amount of L-DOPA ethyl ester, a decarboxylase inhibitor, a microcrystalline cellulose, a starch, and a lubricant, wherein the amount of L-DOPA ethyl ester is between 25–50% by weight, the amount of decarboxylase inhibitor is between 3.0–10% by weight, the amount of microcrystalline cellulose is between 35–60% by weight, the amount of starch is between 3.0–10% by weight and the amount of lubricant is between 0.50–6.0% by weight of the total dispersible tablet.

2. The tablet of claim 1, wherein the decarboxylase inhibitor is carbidopa or benserazide.

3. The tablet of claim 2, wherein the decarboxylase inhibitor is carbidopa.

4. The tablet of claim 3, wherein the carbidopa has a moisture content of between 5.0–10.0%.

5. The tablet of claim 4, wherein the carbidopa has a moisture content of 7.5%.

6. The tablet of claim 1, wherein the microcrystalline cellulose has a moisture content of less than or equal to 5.0%.

7. The tablet of claim 1, wherein the microcrystalline cellulose has a moisture content of less than or equal to 1.5%.

8. The tablet of claim 1, wherein the starch is a pregelatinized starch.

9. The tablet of claim 8, wherein the pregelatinized starch has a moisture content less than or equal to 14%.

10. The tablet of claim 8, wherein the pregelatinized starch has a moisture content of less than or equal to 12%.

11. The tablet of claim 8, wherein the pregelatinized starch has a moisture content of less than or equal to 7%.

12. The tablet of claim 8, wherein the pregelatinized starch has a moisture content of less than or equal to 5%.

13. The tablet of claim 1, wherein the lubricant is selected from the group consisting of talc, sodium stearyl fumarate, magnesium stearate, calcium stearate, hydrogenated castor oil, hydrogenated soybean oil, and polyethylene glycol.

14. The tablet of claim 13, wherein the lubricant is magnesium stearate.

15. The tablet of claim 1, wherein the tablet further comprises a binding agent.

16. The tablet of claim 15, wherein the binding agent is selected from the group consisting of sorbitol, glucose, xylitol, and mannitol.

17. The tablet of claim 16, wherein the binding agent is xylitol or mannitol.

18. The tablet of claim 17, wherein the binding agent is mannitol.

19. The tablet of claim 1, wherein the tablet further comprises an antioxidant.

20. The tablet of claim 19, wherein the antioxidant is selected from the group consisting of tocopheral, sodium metabisulphite, butylated hydroxytoluene, butylated hydroxyanisole, ascorbic acid and sodium ascorbate.

21. The tablet of claim 20, wherein the antioxidant is sodium metabisulphite.

22. The tablet of claim 1, wherein the tablet has a moisture content of between 2.5% and 3.5%.

23. The tablet of claim 1, wherein the L-DOPA ethyl ester is L-DOPA ethyl ester derived from pharmaceutically acceptable, crystalline, non-hygroscopic L-DOPA ethyl ester of at least ninety-seven percent purity and containing less than one percent by weight L-DOPA, characterized in that the amount of L-DOPA ethyl ester decreases by less than four percent after one month at forty degrees Celsius.

24. A dispersible tablet comprising L-DOPA ethyl ester in an amount of between 25–50% by weight, carbidopa in an amount of between 3.0–10% by weight, microcrystalline cellulose in an amount of between 35–60% by weight, starch in an amount of between 3.0–10% by weight, magnesium stearate in an amount of between 0.50–3.0% by weight, mannitol in an amount of between 0.0–5.0% by weight, and sodium metabisulfite in an amount of between 0.0–1.0% by weight of the total dispersible tablet.

25. A dispersible tablet of claim 24, wherein the microcrystalline cellulose comprises:
   (a) a first microcrystalline cellulose with a moisture content of less than or equal to 5%, and
   (b) a second microcrystalline cellulose with a moisture content of less than or equal to 1.5%, wherein the first microcrystalline cellulose is different from the second microcrystalline cellulose; and
wherein the starch comprises:
   (c) a first starch with a moisture content of less than or equal to 12%, and
   (d) a second starch with a moisture content of less than or equal to 5%, wherein the first starch is different from the second starch.

26. A dispersible tablet of claim 24, comprising L-DOPA ethyl ester in an amount of between 29–48% by weight, carbidopa in an amount of between 4.5–7.2% by weight, microcrystalline cellulose in an amount of between 38–56% by weight, starch in an amount of between 4.7–8.3% by weight, magnesium stearate in an amount of between 0.69–2.1% by weight, mannitol in an amount of between 0.0–2.7%, by weight, and sodium metabisulfite in an amount of between 0.0–0.84% by weight of the total dispersible tablet.

27. A dispersible tablet of claim 26, wherein the microcrystalline cellulose comprises:
   (a) a first microcrystalline cellulose with a moisture content of less than or equal to 5%, and
   (b) a second microcrystalline cellulose with a moisture content of less than or equal to 1.5%, wherein the first microcrystalline cellulose is different from the second microcrystalline cellulose; and
wherein the starch comprises:
   (c) a first starch with a moisture content of less than or equal to 12%, and
   (d) a second starch with a moisture content of less than or equal to 5%, wherein the first starch is different from the second starch.

28. A dispersible tablet of claim 27, comprising microcrystalline cellulose with moisture content of less than or equal to 5% in an amount of between 19–22% by weight; microcrystalline cellulose with moisture content of less than or equal to 1.5% in an amount of between 25–36% by weight; starch with moisture content of up to 12% in an amount of between 2.0–4.5% by weight; and starch with moisture content of less than or equal to 5% in an amount of between 1.0–4.5% by weight of the total dispersible tablet.

29. A dispersible tablet of claim 26, comprising L-DOPA ethyl ester in an amount of 30% by weight, carbidopa in an amount of 7.0% by weight, microcrystalline cellulose in an amount of 56% by weight, starch in an amount of 5.4% by weight, and magnesium stearate in an amount of 2.1% by weight of the total dispersible tablet.

30. A dispersible tablet of claim 29, wherein the microcrystalline cellulose comprises:
   (a) a first microcrystalline cellulose with a moisture content of less than or equal to 5%, and
   (b) a second microcrystalline cellulose with a moisture content of less than or equal to 1.5%, wherein the first microcrystalline cellulose is different from the second microcrystalline cellulose; and
wherein the starch comprises:
   (c) a first starch with a moisture content of less than or equal to 12%, and
   (d) a second starch with a moisture content of less than or equal to 5%, wherein the first starch is different from the second starch.

31. A dispersible tablet of claim 30, comprising microcrystalline cellulose with moisture content of less than or equal to 5% in an amount of 21% by weight; microcrystalline cellulose with moisture content of less than or equal to 1.5% in an amount of 35% by weight; starch with moisture content of less than or equal to 12% in an amount of 4.4% by weight; and starch with moisture content of less than or equal to 5% in an amount of 1.0% by weight of the total dispersible tablet.

32. A dispersible tablet comprising L-DOPA ethyl ester in an amount of between 100–300 mg, carbidopa in an amount of between 25–30 mg, microcrystalline cellulose in an amount of between 150–250 mg, starch in an amount of between 15–35 mg, magnesium stearate in an amount of between 0–15 mg, mannitol in an amount of between 0–10 mg, and sodium metabisulfite in an amount of between 0–10 mg for a dispersible tablet between 350–600 mg.

33. A dispersible tablet of claim 32, comprising microcrystalline cellulose with moisture content of less than or equal to 5% in an amount of between 10–25% by weight, microcrystalline cellulose with moisture content of less than or equal to 1.5% in an amount of between 20–40% by weight, starch with moisture content of less than or equal to 12% in an amount of between 1–5% by weight, and starch with moisture content of less than or equal to 5% in an amount of between 1–5% by weight of the total dispersible tablet.

34. The dispersible tablet of claim 32, comprising L-DOPA ethyl ester in an amount of between 114–285 mg, carbidopa in an amount of between 25–30 mg, microcrystalline cellulose in an amount of between 200–230 mg, starch in an amount of between 20–32 mg, magnesium stearate in an amount of between 2.6–10.0 mg, mannitol in an amount of between 0–10 mg, and sodium metabisulfite in an amount of between 0.0–2.0 mg for a dispersible tablet between 376–390 mg.

35. A dispersible tablet of claim 34, wherein the microcrystalline cellulose comprises:
   (a) a first microcrystalline cellulose with a moisture content of less than or equal to 5%, and
   (b) a second microcrystalline cellulose with a moisture content of less than or equal to 1.5%, wherein the first microcrystalline cellulose is different from the second microcrystalline cellulose; and
wherein the starch comprises:
   (c) a first starch with a moisture content of less than or equal to 12%, and
   (d) a second starch with a moisture content of less than or equal to 5%, wherein the first starch is different from the second starch.

36. The dispersible tablet of claim 35, wherein the amount of microcrystalline cellulose with moisture content of less than or equal to 5% is between 79–80 mg; wherein the amount of microcrystalline cellulose with moisture content of less than or equal to 1.5% is between 120–135 mg; wherein the amount of starch with moisture content of less than or equal to 12% is between 8–17 mg; and wherein the amount of starch with moisture content of less than or equal to 5% is between 4–17 mg for a dispersible tablet between 376–384 mg.

37. The dispersible tablet of claim 34, comprising L-DOPA ethyl ester in an amount of 114 mg, carbidopa in an amount of 27 mg, microcrystalline cellulose in an amount of 214 mg, starch in an amount of 21 mg, and magnesium stearate in an amount of 8.0 mg for a dispersible tablet of 384 mg.

38. A dispersible tablet of claim 37, wherein the microcrystalline cellulose comprises:
   (a) a first microcrystalline cellulose with a moisture content of less than or equal to 5%, and
   (b) a second microcrystalline cellulose with a moisture content of less than or equal to 1.5%, wherein the first microcrystalline cellulose is different from the second microcrystalline cellulose; and
wherein the starch comprises:
   (c) a first starch with a moisture content of less than or equal to 12%, and
   (d) a second starch with a moisture content of less than or equal to 5%, wherein the first starch is different from the second starch.

39. The dispersible tablet of claim 38, wherein the amount of microcrystalline cellulose with moisture content of less than or equal to 5% is 79 mg; wherein the amount of microcrystalline cellulose with moisture content of less than or equal to 1.5% is 135 mg; wherein the amount of starch with moisture content of less than or equal to 12% is 17 mg; and wherein the amount of starch with moisture content of less than or equal to 5% is 4 mg for a dispersible tablet of 384 mg.

40. The dispersible tablet of claim 38, wherein
   (a) the first microcrystalline cellulose is present in an amount of about 79 mg;
   (b) the second microcrystalline cellulose is present in an amount of about 135 mg;
   (c) the first starch is present in an amount of about 17 mg; and
   (d) the second starch is present in an amount of about 4 mg.

41. The dispersible tablet of claim 32, wherein the microcrystalline cellulose comprises:
   (a) a first microcrystalline cellulose with a moisture content of less then or equal to 5%, and
   (b) a second microcrystalline cellulose with a moisture content of less than or equal to 1.5%, wherein the first microcrystalline cellulose is different from the second microcrystalline cellulose; and
wherein the starch comprises:
   (c) a first starch with a moisture content of less than or equal to 12%, and
   (d) a second starch with a moisture content of less than or equal to 5%, wherein the first starch is different from the second starch.

42. The dispersible tablet of claim 41, which comprises microcrystalline cellulose with moisture content of less than or equal to 5% in an amount of between 75–85 mg;

microcrystalline cellulose with moisture content of less than or equal to 1.5% in an amount of between 100–200 mg; starch with moisture content of less than or equal to 12% in an amount of between 5–20 mg; and starch with moisture content of less than or equal to 5% in an amount of between 3–25 mg for a dispersible tablet between 350–600 mg.

43. A method of preparing a dispersible tablet comprising the steps of:
   (a) admixing L-DOPA ethyl ester, a filler, and a disintegrant to form a L-DOPA ethyl ester mixture;
   (b) granulating a decarboxylase inhibitor mixture comprising a decarboxylase inhibitor, a disintegrant, and a filler;
   (c) admixing the L-DOPA ethyl ester mixture of step (a) and the decarboxylase inhibitor mixture of step (b) with a filler, a disintegrant, and a lubricant; and
   (d) compressing the admixture of step (c) into a dispersible tablet;
wherein the amount of L-DOPA ethyl ester is between 25–50%, the amount of decarboxylase inhibitor is between 3.0–10%, the amount of filler is between 35–60%, the amount of disintegrant is between 3.0–10%, and the amount of lubricant is between 0.5–3.0% by weight of the total dispersible tablet.

44. The method of claim 43, wherein the admixing in step (c) is performed by first mixing the L-DOPA ethyl ester mixture of step (a) with the decarboxylase inhibitor mixture of step (b), then adding the filler, the disintegrant, and the lubricant.

45. The method of claim 43, wherein the decarboxylase inhibitor is carbidopa or benzerazide.

46. The method of claim 45, wherein the decarboxylase inhibitor is carbidopa.

47. The method of claim 43, wherein the fillers of steps (a), (b), and (c) are selected from a group consisting of corn starch, glucose, various natural gums, methylcellulose, carboxymethyl cellulose, microcrystalline cellulose, calcium phosphate, calcium carbonate, calcium sulfate kaolin, sodium chloride, powdered cellulose, sucrose, mannitol and starch.

48. The method of claim 47, wherein, the filler of steps (a), (b), and (c) is a microcrystalline cellulose.

49. The method of claim 48, wherein the microcrystalline cellulose of step (a) has a moisture content no greater than 5%.

50. The method of claim 48, wherein the microcrystalline cellulose of step (b) and (c) has a moisture content no greater than 1.5%.

51. The method of claim 43, wherein the disintegrant of steps (a), (b), and (c) is selected from the group consisting of kaolin, starch, pregelatinized starch, powdered sugar, sodium starch glycolate, crosscarmelose sodium, carboxymethyl cellulose, microcrystalline cellulose and sodium alginate.

52. The method of claim 51, wherein the disintegrant of steps (a), (b), and (c) is pregelatinized starch.

53. The method of claim 43, wherein the lubricant of step (c) is selected from the group consisting of talc, sodium stearyl fumarate, magnesium stearate, calcium stearate, hydrogenated castor oil, hydrogenated soybean oil and polyethylene glycol.

54. The method of claim 53, wherein the lubricant of step (c) is magnesium stearate.

55. The method of claim 43, wherein the L-DOPA ethyl ester mixture of step (a) and the carbidopa mixture of step (b) further comprise a binding agent.

56. The method of claim 55, wherein the binding agent is selected from the group consisting of sorbitol, glucose, xylitol, and mannitol.

57. The method of claim 56, wherein the binding agent is mannitol.

58. The method of claim 43, wherein the L-DOPA ethyl ester mixture of step (a) further comprises an antioxidant.

59. The method of claim 58, wherein the antioxidant of step (a) is selected from the group consisting of tocopheral, sodium metabisulphite, butylated hydroxytoluene, butylated hydroxyanisole, ascorbic acid and sodium ascorbate.

60. The method of claim 59, wherein the antioxidant of step (a) is sodium metabisulfite.

61. A method of preparing a dispersible tablet comprising the steps of:
   (a) admixing L-DOPA ethyl ester, a microcrystalline cellulose, and a starch to form a L-DOPA ethyl ester mixture;
   (b) granulating a decarboxylase inhibitor mixture comprising carbidopa, a starch, and a microcrystalline cellulose;
   (c) admixing the L-DOPA ethyl ester mixture of step (a) and the carbidopa mixture of step (b) with a microcrystalline cellulose, a starch, and a magnesium stearate; and
   (d) compressing the admixture of step (c) into a dispersible tablet;
wherein the amount of L-DOPA ethyl ester is between 25–50% by weight, the amount of carbidopa is between 3.0–10% by weight, the amount of microcrystalline cellulose is between 35–60% by weight, the amount of starch is between 3.0–10% by weight, the amount of magnesium stearate is between 0.5–3.0% by weight, and further comprising an amount of an excipient between 0.0–5.0% by weight, and an amount of antioxidant between 0.0–2.5% by weight of the total dispersible tablet.

62. The method of claim 61, wherein the excipient is a binding agent selected from the group consisting of sorbitol, glucose, xylitol, and mannitol and wherein the antioxidant is selected from the group consisting of tocopheral, sodium metabisulphite, butylated hydroxytoluene, butylated hydroxyanisole, ascorbic acid and sodium ascorbate.

63. The method of claim 62, wherein the amount of L-DOPA ethyl ester, is between 29–48% by weight, the amount of carbidopa is between 4.5–7.2% by weight, the amount of microcrystalline cellulose is between 38–56% by weight, the amount of starch is between 4.7–8.3% by weight, the amount of magnesium stearate is between 0.69–2.1% by weight, the amount of mannitol is between 0.0–2.7% by weight, and the amount of sodium metabisulfite is between 0.0–0.84% by weight of the total dispersible tablet.

64. The method of claim 63, wherein the amount of L-DOPA ethyl ester is 30% by weight, the amount of carbidopa is 7.0% by weight, the amount of microcrystalline cellulose is 56% by weight, the amount of starch is 5.4% by weight, and the amount of magnesium stearate is 2.1% by weight of the total dispersible tablet.

65. A dispersible tablet prepared by the method of claim 43.

* * * * *

UNITED STATES PATENT AND TRADEMARK OFFICE
CERTIFICATE OF CORRECTION

PATENT NO. : 6,376,545 B1
DATED : April 23, 2002
INVENTOR(S) : Levin et al.

It is certified that error appears in the above-identified patent and that said Letters Patent is hereby corrected as shown below:

<u>Title page,</u>
Item [75], Inventor please add: -- Omer Tsipori, Petach-Tikva (IL) --

Signed and Sealed this

Third Day of September, 2002

Attest:

Attesting Officer

JAMES E. ROGAN
Director of the United States Patent and Trademark Office